United States Patent [19]

Mrozik

[11] 4,062,952

[45] Dec. 13, 1977

[54] SUBSTITUTED BENZENEDISULFONAMIDES AS ANTHELMINTICS

[75] Inventor: Helmut H. Mrozik, Matawan, N.J.

[73] Assignee: Merck & Co., Inc., Rahway, N.J.

[21] Appl. No.: 634,561

[22] Filed: Nov. 24, 1975

[51] Int. Cl.$^2$ .................. C07C 143/80; A01N 9/16
[52] U.S. Cl. .................. 424/228; 260/397.7 DS; 260/556 S; 429/321
[58] Field of Search .............. 260/556 S, 397.7 DS; 424/321, 228

[56] References Cited

U.S. PATENT DOCUMENTS

| | | | |
|---|---|---|---|
| 2,965,655 | 12/1960 | Novello | 260/556 S X |
| 2,965,656 | 12/1960 | Novello | 260/556 S X |
| 2,965,675 | 12/1960 | Novello | 260/556 S X |
| 3,009,910 | 11/1961 | Ziegler | 260/556 S X |
| 3,139,381 | 6/1964 | Novello | 260/556 S X |
| 3,163,644 | 12/1964 | de Stevens et al. | 260/555 S X |
| 3,164,517 | 1/1965 | Novello | 260/556 S X |
| 3,164,588 | 1/1965 | Irons et al. | 260/556 S X |
| 3,252,975 | 5/1966 | de Stevens et al. | 260/556 S X |
| 3,829,487 | 8/1974 | Mrozik | 260/556 B X |
| 4,001,406 | 1/1977 | Mrozik | 424/228 |
| 4,005,199 | 1/1977 | Mrozik | 424/228 |

*Primary Examiner*—Allen B. Curtis
*Assistant Examiner*—Thomas A. Weltz
*Attorney, Agent, or Firm*—David L. Rose; J. Jerome Behan

[57] ABSTRACT

Substituted benzenedisulfonamides are disclosed, which are active anthelmintic agents being particularly useful against fascioliasis in sheep and cattle. Specifically the active compounds are 4-amino-1,3-benzenedisulfonamide compounds substituted at the 6-position with certain alkyl groups. Compositions and methods containing the novel substituted benzenedisulfonamides for use in anthelmintic therapy, particularly against liver fluke are also disclosed.

12 Claims, No Drawings

SUBSTITUTED BENZENEDISULFONAMIDES AS ANTHELMINTICS

DESCRIPTION OF THE PRIOR ART

Simple 6-alkyl substituted-4-amino-1,3-benzenedisulfonamides, wherein the alkyl group is methyl or ethyl, are known in the art. Such compounds are not contemplated by the instant invention, however, and in fact these compounds are inactive against fasciola. The instant 6-position alkyl groups are active fasciolicidal agents, and this activity could not be predicted from an analysis of the prior art.

SUMMARY OF THE INVENTION

The anthelmintic compounds of the invention are classified generally as benzenedisulfonamides. Specifically they may be described as 4-amino-6-alkyl substituted-1,3-benzenedisulfonamides. Said compounds have significant and unexpected anthelmintic activity and in particular demonstrate high activity against fasciola or liver fluke in animals.

Thus, it is an object of this invention to provide for novel anthelmintic compounds. A further object of this invention is provide for novel substituted benzenedisulfonamide compounds which have significant anthelmintic and fasciolicidal activity. A still further object of this invention is to provide for processes for the preparation of said novel substituted benzenedisulfonamide. Another object is to provide for compositions and methods of treatment which contain said novel substituted benzenedisulfonamides and which are useful in the prevention and treatment of fascioliasis. Further objects will become apparent from the following description.

DESCRIPTION OF THE INVENTION

The novel fasciolicidal compounds of this invention are best represented by the following structural formula:

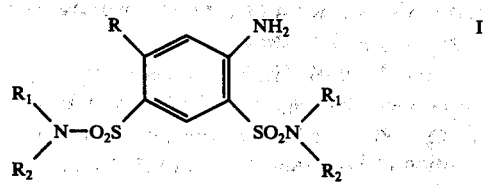

wherein each $R_1$ and $R_2$ is independently hydrogen or loweralkyl; and R is a secondary alkyl group of from 3 to 6 carbon atoms, R is also a cycloalkyl group of 5 or 6 members, or phenyl.

The term "loweralkyl" when used in the instant specification refers to those alkyl groups of from 1 to 6 carbon atoms of either a straight or branched configuration such as methyl, ethyl, propy, butyl, pentyl, hexyl, isopropyl, tert-butyl and the like.

The preferred embodiments of this invention are realized when $R_1$ and $R_2$ are all hydrogen and R is a secondary alkyl group as above defined. Exemplary of such secondary alkyl groups are the isopropyl, isobutyl, 3-pentyl and 2-pentyl groups. The isopropyl group is particularly preferred.

Specific compounds representative, but not restrictive of the scope of this invention are as follows:

4-amino-6-isopropyl-1,3-benzenedisulfonamide
4-amino-6-isobutyl-1,3-benzenedisulfonamide
4-amino-6-(2-butyl)-1,3-benzenedisulfonamide
4-amino-6-(2-pentyl)-1,3-benzenedisulfonamide
4-amino-6-phenyl-1,3-benzenedisulfonamide
4-amino-6-cyclopentyl-1,3-benzenedisulfonamide
4-amino-6-cyclohexyl-1,3-benzenedisulfonamide The compounds wherein R is a secondary alkyl or a cycloalkyl group as above defined are prepared from benzene starting materials which are already substituted with the appropriate R substituent. Preferably the starting material is a 3-R substituted nitro benzene. The compounds of this invention are then prepared as follows:

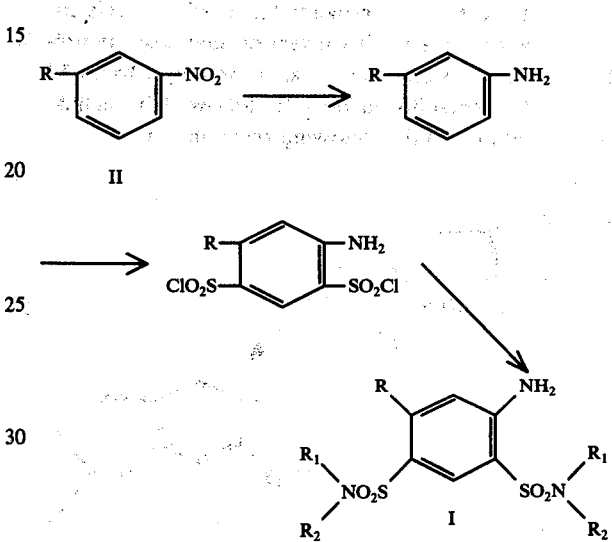

wherein R, $R_1$ and $R_2$ are as previously defined.

In the foregoing procedures the nitrobenzene starting material is reduced using standard reduction techniques preferably a catalytic reduction such as an active metal in acid medium. Powdered iron in hydrochloric acid is suitable. Other reduction techniques such as catalytic hydrogenation are also acceptable. The nitrobenzene is preferably dissolved in an organic solvent such as a loweralkanol and heated with the metal catalyst and acid for from 10 minutes to 5 hours. The R-substituted aniline compound is isolated by techniques known to those skilled in this art.

The R-substituted aniline is then reacted with chlorosulfonic acid to prepare the di-sulfonyl chloride compound. The reaction is carried out initially with external cooling due to a possible exothermic reaction as the starting materials and chlorosulfonic acid are combined. Generally the amine is added dropwise or portionwise, over a period of from 5 minutes to 2 hours, to the chlorosulfonic acid maintaining the reaction temperature at from −10° to 10° C. When the reaction is complete, the reaction temperature is raised to from 50° C. to the boiling point of the reaction mixture for from 15 minutes to 4 hours. A solvent is optional and generally employed only when the reaction temperature is below 100° C. It is preferred, however, to run the reaction without a solvent. The R substituted benzenedisulfonyl chloride is recovered from the reaction mixture by procedures known to those skilled in this art.

The benzenedisulfonyl chloride is then reacted with ammonia or a mono- or di-loweralkylamine to form the desired benzenedisulfonamide. The reaction may be carried out with aqueous solutions of ammonia or the mono- or di-loweralkylamine; non aqueous solutions of ammonia or the mono or di-loweralkylamine in any nonreactive organic solvent such as benzene, toluene, ether, chloroform and the like; or the reaction may be carried out in liquid ammonia or the mono- or di-loweralkylamine. The reaction is somewhat exothermic and external cooling is preferred. Temperatures from −75° to 10° C. may be employed initially. The reaction is complete in from 10 minutes to 6 hours at from −30° C. to room temperature following an initial cooling period of from 5 minutes to ½ hour. The product is isolated by techniques known to those skilled in this art.

The compounds of this invention may also be prepared by chlorosulfonating an appropriately substituted o-aminobenzenesulfonamide (III) followed by amination as outlined in the following reaction scheme:

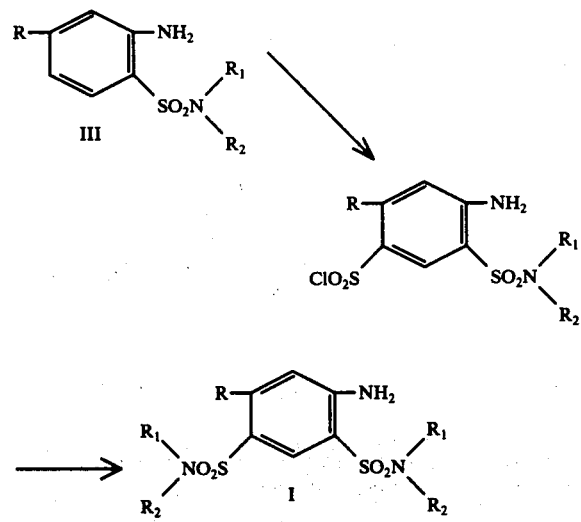

wherein R, $R_1$ and $R_2$ are as previously defined. The chlorosulfonation and amination are carried out employing the techniques and reaction conditions described above. The foregoing process affords products wherein the $NR_1R_2$ group on each of the sulfonamide moieties is different from the other.

The nitrobenzene starting materials are generally known in the prior art or procedures are readily available for their preparation. Occasionally, however, starting materials are available wherein the R-group is para to the nitro rather than meta. In such a case, the following procedure affords the proper meta substituted nitrobenzene (II):

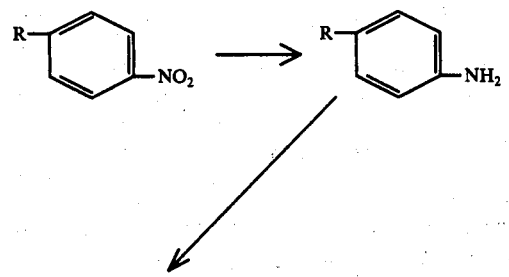

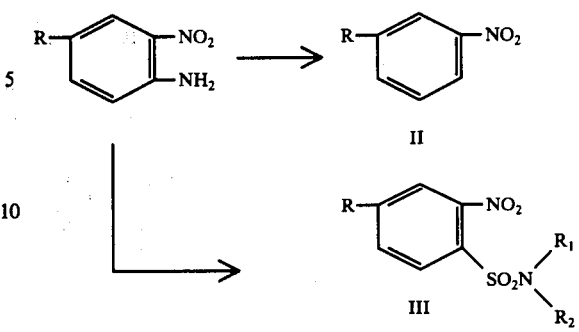

wherein R is as previously defined.

The para-substituted nitrobenzene is reduced to the corresponding aniline compound according to the reduction procedures previously defined.

The aniline compound is nitrated using standard nitrating techniques such as nitric acid or fuming nitric acid. The amine group is preferably protected prior to the nitration with an acyl protecting group. An acyl chloride or anhydride is employed, preferably acetyl chloride or acetic anhydride. The protecting group is removed, using hydrolysis techniques, following the nitration. The nitro aniline is then diazotized. The diazonium salt may be reduced to the meta R-nitrobenzene (II) or it may be used to prepare the monosulfonamide starting material (III).

The nitro aniline is diazotized using acid medium and an alkali metal nitrite preferably sodium nitrite. To reduce the diazonium salt, ethanol is employed. To prepare the sulfonyl chloride, the diazonium salt is treated with sulfur dioxide and cuprous chloride in aqueous acetic acid. The sulfonyl chloride is then reacted with ammonia or a mono- or diloweralkylamine as previously described.

When the R substituent is a phenyl group, a different route must be employed. Chlorosulfonation of the phenyl substituted aniline compound will result in substitution of both the phenyl groups by the chlorosulfonyl group. The following reaction scheme describes the preparation of compounds wherein R is phenyl.

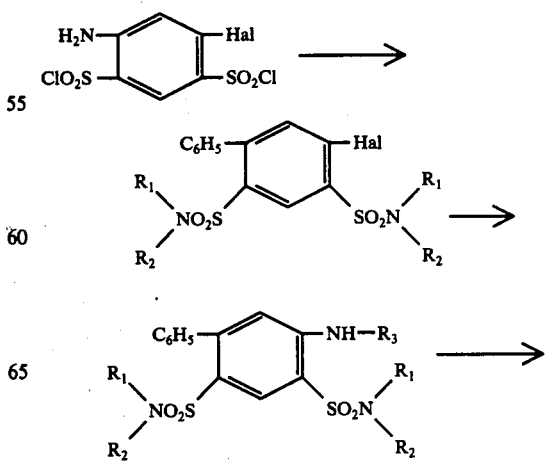

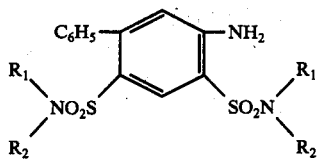

wherein $R_1$ and $R_2$ are as previously defined and $R_3$ is an aralkyl group, preferably furfuryl or benzyl and Hal is a halogen such as fluorine, chlorine or bromine.

In the foregoing procedures m-fluoroaniline is chlorosulfonated by known procedures to obtain the above 4-amino-6-fluoro-1,3-benzene disulfonyl chloride starting materials. This compound is treated with isoamylnitrite in benzene to obtain the 4-phenyl compound. The reaction is conducted using benzene as a solvent as well as a reactant and is complete in from 1 to 10 hours at from room temperature to the reflux temperature of the reaction mixture. This phenyl compound is treated with an $R_1$, $R_2$ amine as previously described to obtain the 4-phenyl-6-fluoro-1,3-benzenedisulfonamide compound.

The fluoro group is converted to the amino group by heating at from 50° to 150° C. with an aralkyl amine, preferably furfurylamine or benzylamine. The reaction is complete in from ½ to 6 hours and the 6-aralkyl amino compound is isolated by techniques known to those skilled in this art. The aralkyl group is removed by treatment with aqueous acid such as hydrochloric acid or by treatment with trifluoroacetic acid for from ½ to 5 hours at from room temperature to 100° C. or hydrogenolysis. The product amino compound is isolated by techniques known to those skilled in this art.

As aforementioned certain simple 6-alkyl-4-amino-1,3-benzenedisulfonamides are disclosed in this art. It has been discovered, however, that such simple alkyl groups are inactive as fasciolicides. In addition it has been surprisingly discovered that secondary alkyl groups, and the other groups contained in the definition of $R_1$ are active fasciolicides. The methyl, ethyl, n-propyl, n-butyl and tert-butyl groups($R_1$=$R_2$=H) have been tested against fascioliasis. In each case the compounds demonstrated no activity against fascioliasis at doses of 100 mg./kg. In addition the secondary alkyl groups isopropyl, isobutyl, and 2-butyl were tested against fascioliasis and were found to have substantial activity. For example the isopropyl compound ($R_1$=$R_2$=H) is active at 100 mg./kg. when tested in rats and sheep. The isobutyl compound is active at 50 mg./kg. when tested in rats and 100 mg./kg. in sheep. The 2-butyl compound is active at 100 mg./kg. in sheep.

In addition substantial activity is seen against fasciola for those compounds wherein R is phenyl, cyclopentyl, cyclohexyl and the like.

The compounds of the present invention have utility in the field of animal therapy. They are effective in both the prevention and cure of both mature and immature liver fluke of the species *Fasciola gigantica* and *Fasciola hepatica*, the common liver fluke in sheep and cattle. The preferred dosage levels depend on the type of compound to be employed, the type of animal to be treated, the particular helminth to be combatted, and the severity of the helmintic infestation. In general, effective fluke eradication is achieved when the compounds are administered in a single dose at dosage levels of from about 10 to 150 mg./kg. of animal body weight and preferably from about 25 to 75 mg./kg. of animal body weight. The compounds of the present invention may be administered in a variety of ways depending upon the particular animal employed, the type of anthelmintic treatment normally given to such animal, the materials employed and the particular helminths being combatted. It is preferred to administer them in anthelmintically effective amounts in a single or divided oral or parenteral dose at a time when fluke infection is apparent or suspected in the animal.

In addition to the inactive ingredients in the composition, said composition may contain one or more other active ingredients which may be selected from the compounds of formula I or from other known anthelmintic agents. Beneficial results are obtained when the compounds of formula I are combined with an anthelmintic agent such as 2-(4-thiazolyl)benzimdiazole (thiabendazole) 5-isopropoxycarbonylamino-2-(4-thiazolyl)benzimidazole (cambendazole) or tetramisole (dl-2,3,5,6-tetrahydro-6-phenylimidazo [2-1-b]thiazole) or other known anthelmintic agents.

In general, compositions containing the active anthelmintic compound are employed. The amounts of the anthelmintic ingredient in the composition as well as the remaining constituents vary according to the type of treatment to be employed, the host animal and the particular helmintic infestation being treated. In general, however, compositions suitable for oral administration, containing a total weight percent of the active compound or compounds ranging from 0.01 to 95% will be suitable with the remainder of the compositions being any suitable carrier or vehicle. A number of modes of treatment may be employed and each to some extent determines the general nature of the composition. For example, the anthelmintic compounds may be administered to domesticated animals in a unitary oral dosage form such as a tablet, bolus, paste, capusle or drench; a liquid oil base form suitable for parenteral administration, or they may be compounded as a feed premix to be later admixed with the animal's food. When the compositions are to be solid unit dosage forms as in tablets, capsules, or boluses, the ingredients other than the active compounds may be any other non-toxic vehicle convenient in the preparation of such forms and preferably materials nutritionally suitable such as starch, lactose, talc, magnesium stearate, vegetable gums, and the like. Moreover, when capsules are employed, the active compound may be used in essentially undiluted form, the only extraneous material being that of the capsule casing itself which may be hard or soft gelation or any other orally acceptable encapsulating material. When the dosage form is to be used for parenteral administration, the active material is suitably admixed with an acceptable oil base vehicle preferably of the vegetable oil variety such as peanut oil, cotton seed oil, and the like. In all such forms, that is, in tablets, boluses, capsules, and oil base formulations; the active compound conveniently ranges from about 5 to 95% by weight of the total composition.

When the unit dosage form is to be in the form of a drench, the anthelmintic agents may be mixed with agents which will aid in the subsequent suspending of the active compounds in water such as bentonite, clays, water soluble starches, cellulose derivatives, gums, surface active agents and the like to form a dry pre-drench composition, and this pre-drench composition is added to water just before use. In the pre-drench formulation, in addition to the suspending agent, such ingredients as preservatives, anti-foam compounds, or other suitable diluents or solvents may be employed. Such a dry product may contain as much as 95% by weight of the active compound, the rest being excipient. preferably, the solid composition contains from 30 to 95% by weight of the active compound. Enough water should be added to the solid product to provide proper dosage level with a convenient amount of liquid for a single oral dose. The commonly used measure in the field is 1 fluid ounce of material and thus that 1 fluid ounce of material should contain enough of the anthelmintic compound to provide an effective dosage level. Liquid drench formulations containing from 10 to 50% by weight of dry ingredients will, in general, be suitable with a preferred range being from 15 to 25 weight percent.

When the compositions are intended to be used in feeds, feed supplements or feed premixes, they will be mixed with suitable ingredients of the animal's nutrient ration. Solid orally ingestible carriers normally used for such purposes such as distillers dried grains, corn shells, citrus meal, attapulgus clay, wheat shorts, molasses solubles, corn cob meal, vegetable substances, toasted dehulled soya flour, soya bean meal feed, antibiotic mycelia, soya grits, crushed limestone and the like are all suitable. The active compounds are intimately dispersed or admixed throughout the active solid carrier by methods as grinding, melting or tumbling. By selecting a proper diluent and by altering the ratio of carrier to active ingredient, compositions of any desired concentration may be prepared. Feed supplement formulations containing from about 5 to 30% of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration desired for controlling or treating the helminth infection by way of animal ration. Although the preferred level in feeds will depend on the particular compounds being employed, the active compounds of this invention are normally fed at levels of 0.01 to 3%. As stated above, animals are preferably treated at a time when the infestation is apparent or suspected and the most preferred method of treatment is with oral doses. Thus, administration of medicated feed is not preferred but may be employed. Similarly, the amounts of drug present in the feed may be reduced to levels in the order of 0.01% to 0.5% by weight. Based on the weight of the feed and the medicated feed administered over prolonged periods. This could be in the nature of a preventive of prophylactic measure. Another method of administering the compounds of this invention to animals whose feeds are conveniently pelleted such as sheep is to incorporate them directly into the pellets. For instance, the anthelmintic compounds are readily incorporated in the nutritionally adequate alfalfa pellets at levels of 2 to 10 g. per pound for therapeutic use and lower levels for prophylactic use, and such pellets fed to the animals.

Examples of compositions suitable for administration to animals are:

A typical bolus composition is as follows:

| | |
|---|---|
| 4-Amino-6-isopropyl-1,3-benzene-disulfonamide | 7.0 g. |
| Dicalcium phosphate | 1.0 g. |
| Starch | 0.7 g. |

-continued

| | |
|---|---|
| Guar gum | 0.16 g. |
| Talc | 0.11 g. |
| Magnesium stearate | 0.028 g. |

A typical drench composition is as follows:

| | |
|---|---|
| 4-Amino-6-isobutyl-1,3-benzene-disulfonamide | 5.0 g. |
| Benzalkonium chloride | 5.6 ml. |
| Antifoam emulsion | 0.06 g. |
| Hydroxyethyl cellulose | 0.3 g. |
| Sodium phosphate | 0.3 ml. |
| Water | q.s. to 30 ml. |

Examples of typical feed premix supplements are as follows:

| | | |
|---|---|---|
| A. | 4-Amino-6-(2-butyl)-1,3-benzene-disulfonamide | 10 lbs. |
| | Wheat shorts | 90 lbs. |
| B. | 4-Amino-6-phenyl-1,3-benzene-disulfonamide | 15 lbs. |
| | Ground oyster shells | 40 lbs. |
| | Citrus meal | 45 lbs. |
| C. | 4-Amino-6-(2-pentyl)-1,3-benzene-disulfonamide | 10 lbs. |
| | Corn meal | 90 lbs. |
| D. | 4-Amino-6-(3-pentyl)-1,3-benzene-disulfonamide | 15 lbs. |
| | Wheat shorts | 50 lbs. |
| | Corn meal | 35 lbs. |

The above feed premix supplements are combined with the animal's regular feed, intimately mixing therewith such that the final concentration of the active ingredient is from 0.01 to 3% by weight.

EXAMPLE 1

4-Amino-6-isopropyl-1,3-benzenedisulfonamide

A. 4-Isopropylnitrobenzene

To 100 g. of cumene at 10° C. is slowly added over a period of 2.5 hours to a mixture of 70.5 ml. of concentrated nitric acid and 109 ml. of concentrated sulfuric acid. The reaction mixture is stirred at 5° to 10° C. for 1 hour following the addition. The reaction mixture is poured onto 250 ml. of ice water and extracted with ether. The ether is dried and evaporated in vacuo and the residue distilled at 9.5 to 10.5 mm./Hg. The fraction boiling at 130° C. is taken and used as is in the next step.

B. 4-Isopropylaniline 22G. of the material isolated from part A is combined with 300 ml. of 50% aqueous ethanol and combined with 23 g. of iron powder with stirring. The reaction mixture is brought to reflux and 13.5 ml. of a solution of 5.2 ml. of concentrated hydrochloric acid in 25 ml. 50% aqueous ethanol is added slowly. The suspension is stirred for ½ hour and made basic with 2.5 N sodium hydroxide solution. The reaction mixture is steam distilled and the distillate extracted with chloroform, dried and evaporated in vacuo affording 20 g. of 4-isopropylaniline.

C. 4-Isopropyl-2-nitroaniline 20.0 G. (0.148 moles) of 4-isopropylaniline is added with stirring to 75 ml. of acetic anhydride at from 20° to 45° C. The reaction mixture is stirred at 35° C. for 1 hour. 11 Ml. of fuming nitric acid (specific gravity 1.5) is added at a temperature of from 25° to 35° C. over a period of 20 minutes and stirred for 3 hours. The acid mixture is added to a mixture of 180 ml. of water, 45 ml. of concentrated sulfuric acid and 142 ml. of ethanol with stirring. The reaction mixture is stirred overnight at room temperature, refluxed for 2 hours, neutralized with saturated sodium carbonate solution and extracted with chloroform. The chloroform layer is dried and evaporated in vacuo affording 35 g. of a dark orange oil which is used as is in the next step.

D. 3-Isopropylnitrobenzene 3.56 G. of 4-isopropylnitroaniline is dissolved in 580 ml. of ethanol and stirred. 30.4 Ml. of concentrated sulfuric acid is added dropwise. The reaction mixture is heated to reflux and a solution of 16 g. of sodium nitrite in 25 ml. of water is added dropwise over 5 minutes. Heating is continued for 1 hour and then the reaction mixture is allowed to cool to room temperature. 250 Ml. of water and 1200 ml. of chloroform is added, the layers are separated and the water layer is extracted with an additional 230 ml. of chloroform. The chloroform layers are combined, washed with 250 ml. of water, dried over sodium sulfate and the solvent is removed by distillation through a short vigreau column at atmosphere pressure. The residue is vacuum distilled at from 8.6 to 9.0 mm. of Hg. The fraction taken at 112° to 128° C. is used as is in the next step.

E. 3-Isopropylaniline

2 G. (0.127 mole) of 3-isopropylnitrobenzene is dissolved in 300 ml. of 50% aqueous ethanol and 23 g. of iron powder is added with good stirring. The reaction mixture is brought to reflux and 13.5 ml. of a solution of 5.2 ml. of concentrated hydrochloric acid in 25 ml. of 50% aqueous ethanol is added while maintaining reflux and stirring. After ½ hour of stirring, the reaction mixture is made basic with 2.5 N sodium hydroxide and steam distilled. The distillate is extracted with chloroform and the chloroform layer dried and concentrated by distillation through a short vigreau column under atmospheric pressure. The residue is vacuum distilled. One fraction with boiling point of 117°–118° C. at 18 mm. Hg. contains 15.14 g. of 3-isopropylaniline which is suitable for use in the next step without further purification.

F. 4-Amino-6-isopropyl-1,3-benzenedisulfonamide 14.7 Ml. (25.6 g., 0.22 mole) of chlorosulfonic acid is cooled to 4° C. and added to 2.7 g. (0.02 mole) of 3-isopropylaniline dropwise over 5 minutes maintaining the temperature below 10° C. with stirring. The temperature is rapidly brought to 120° to 130° C. and maintained at this temperature for 2 ½ hours. The reaction mixture is cooled to 2° C. and 5.8 ml. (9.2 g.) of thionylchloride is added. Then it is heated on an oil bath at 80° C. for 1 ½ hours, cooled in an ice bath and added carefully to 50 g. of ice with vigorous stirring with further additions of ice as required to maintain the temperature at 10° C. The aqueous mixture is extracted with methylene chloride, the methylene chloride layer washed with water and dried over magnesium sulfate. The methylene chloride solution is concentrated in vacuo affording 7 g. of a brown oil. The oil is dissolved in 15 ml. of methylene chloride and added in portions of 75 ml. of liquid ammonia with stirring. The ammonia is allowed to evaporated and 10 ml. of water is added and the solution is acidified slightly with 2.5 N hydrochloric acid. The suspension is allowed to age for 10 hours, filtered, washed with water and dried in vacuo at 50° C. affording 4.84 g. of a tan solid. The solid is recrystallized from hot water giving 4-amino-6-isopropyl-1,3-benzenedisulfonamide m.p. 185° to 186° C.

Following the foregoing procedures and using the appropriate starting materials the following products are obtained:
4-amino-6-(2-butyl)-1,3-benzenedisulfonamide m.p. 100° to 115° C. (as ethanol solvate)
4-amino-6-isobutyl-1,3-benzenedisulfonamide m.p. 195° to 196° C.
4-amino-6-cyclopentyl-1,3-benzenedisulfonamide m.p. 176° C.
4-amino-6-cyclohexyl-1,3-benzenedisulfonamide m.p. 219° to 220° C.

EXAMPLE 2

4-Amino-6-phenyl-1,3-benzenedisulfonamide

A. 4-Fluoro-6-phenyl-1,3-benzenedisulfonamide

A solution of 9.24 g. of 4-amino-6-fluoro-1,3-benzenedisulfonylchloride is stirred at 25° C. of benzene. 4.92 G. of isoamylnitrite is added, the reaction mixture heated to 70° C. and stirred for 3 hours. A second 4.92 g. (5.7 ml.) of isoamylnitrite is then added and the mixture heated for another 3 hours. The reaction mixture is concentrated in vacuo affording a reddish gum which is identified by mass spectral analysis as 4-fluoro-6-phenyl-1,3-benzenedisulfonylchloride. This material is dissolved in 50 ml. of methylene chloride and added to 300 ml. of liquid ammonia. The reaction mixture is left at room temperature overnight and the residual ammonia and methylene chloride removed in a stream of nitrogen. Water is added to the residue which is acidified with dilute hydrochloric acid and extracted with ethyl acetate. The ethyl acetate solution is concentrated to a volume of 150 ml. and added to 50 g. of silica gel. The mixture is concentrated in vacuo, suspended in methylene chloride, and added to a chromatography column of 400 g. of silica gel. Fractions are obtained by elution with methylene chloride/ethylacetate mixtures with increasing concentration of ethylacetate of from 5 to 15%. The fractions containing the desired 4-fluoro-6-phenyl-1,3-benzenedisulfonamide are combined and concentrated in vacuo affording a yellow gum. Crystallization from ether/methylene chloride affords 2.27 g. of a crystalline material with a m.p. of 170° to 176° C. Recrystallization from ether affords 1.69 g. of 4-fluoro-6-phenyl-1,3-benzenedisulfonamide with a m.p. of 174° to 175° C.

B. 4-Amino-6-phenyl-1,3-benzenedisulfonamide 1.68 G. of 4-fluoro-6-phenyl-1,3-benzenedisulfonamide and 3.1 g. of furfurylamine is heated to 95° C. for 1 ½ hours. This mixture is cooled in ice, diluted with 30 ml. of ice water and acidified with acetic acid affording a brown precipitate of 4-furfurylamino-6-phenyl-1,3-benzenedisulfonamide which is collected by filtration and dried affording 2.14 g. of material with a m.p. of 168° to 171° C. This material is stirred with 22 ml. of trifluoroacetic acid at room temperature for 1 hour. The trifluoroacetic acid is removed in vacuo and the residue treated with 100 ml. of water and extracted with ethylacetate. The ethylacetate is dried and evaporated to dryness in vacuo affording 2.6 g. of material which is purified on a chromatography column of silica gel affording 1.6 g. of a light foam. This material is crystallized from water affording 4-amino-6-phenyl-1,3-benzenedisulfonamide with a m.p. of 197° to 198° C.

What is claimed is:

1. A compound having the formula:

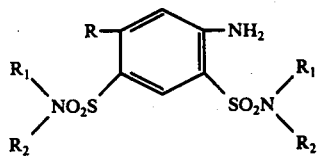

wherein each $R_1$ and $R_2$ is independently hydrogen or loweralkyl; and R is a secondary alkyl group of from 3 to 6 carbon atoms; and R is also cycloalkyl of 5 or 6 carbon atoms, or phenyl.

2. The compound of claim 1 wherein $R_1$ and $R_2$ are hydrogen and R is a secondary alkyl group of from 3 to 6 carbon atoms.

3. The compound of claim 2 which is 4-amino-6-isopropyl-1,3-benzenedisulfonamide.

4. The compound of claim 2 which is 4-amino-6-isobutyl-1,3-benzenedisulfonamide.

5. The compound of claim 2 which is 4-amino-6-(3-pentyl)-1,3-benzendisulfonamide.

6. The compound of claim 2 which is 4-amino-6-(2-pentyl)-1,3-benzenedisulfonamide.

7. The compound of claim 2 which is 4-amino-6-(2-butyl)-1,3-benzenedisulfonamide.

8. The compound of claim 2 which is 4-amino-6-cyclohexyl-1,3-benzenedisulfonamide.

9. The compound of claim 2 which is 4-amino-6-cyclopentyl-1,3-benzenedisulfonamide.

10. The compound of claim 2 which is 4-amino-6-phenyl-1,3-benzenedisulfonamide.

11. A method for the prevention and treatment of liver fluke infection which comprises administering to an animal so infected or suspected of being so infected, with a fasciolicidally effective amount of a compound having the formula:

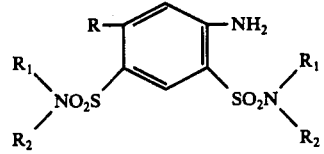

wherein each $R_1$ and $R_2$ is independently hydrogen or loweralkyl; and R is a secondary alkyl group of from 3 to 6 carbon atoms; cycloalkyl of 5 or 6 carbon atoms, or phenyl.

12. A composition for the administration to animals infected with or suspected of being infected with fascioliasis, which comprises an inert carrier and a fasciolicidally effective amount of a compound having the formula:

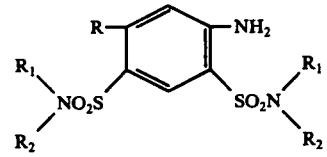

wherein each $R_1$ and $R_2$ is independently hydrogen or loweralkyl; and R is a secondary alkyl group of from 3 to 6 carbon atoms; cycloalkyl of 5 or 6 carbon atoms, or phenyl.

* * * * *